United States Patent [19]
Velazquez et al.

[11] Patent Number: 5,523,571
[45] Date of Patent: Jun. 4, 1996

[54] VERSATILE RECONFIGURABLE GANTRY FOR USE IN SCINTILLATION CAMERA SYSTEMS

[75] Inventors: Herb F. Velazquez, Lombard; David A. Yunker, Cicero; Darryl Hrdina, Mount Prospect, all of Ill.

[73] Assignee: Siemens Medical Systems, Inc., Iselin, N.J.

[21] Appl. No.: 414,853

[22] Filed: Mar. 31, 1995

[51] Int. Cl.$^6$ .............................. G01T 1/163; G01T 1/166
[52] U.S. Cl. .................... 250/363.05; 250/363.08
[58] Field of Search ...................... 250/363.04, 363.05, 250/363.08; 378/11, 15

[56] References Cited

U.S. PATENT DOCUMENTS 5,444,252  8/1995  Hug et al. ........................ 250/363.03 X

*Primary Examiner*—Carolyn E. Fields
*Assistant Examiner*—Edward J. Glick
*Attorney, Agent, or Firm*—Mark H. Jay

[57] ABSTRACT

First and second scintillation camera detectors are provided and are mounted, respectively, to first and second yoke assemblies. The first yoke assembly is mounted to a ring gear which is rotatable within a vertical plane about a horizontal axis. The second yoke assembly is mounted to an annulus which is located within the ring gear and which is rotatable within the plane and about the axis. A rotating device is provided for rotating the ring gear in the plane and about the axis and a locking device is also provided for locking the first and second yoke assemblies together, whereby the first and second yoke assemblies rotate together when they are locked together and the first yoke assembly is being rotated by the rotating device. Advantageously, each detector is pivotally secured to its corresponding yoke assembly and each of the detectors is radially movable towards and away from the axis of the gantry. Further advantageously, the entire gantry is laterally moveable.

8 Claims, 8 Drawing Sheets

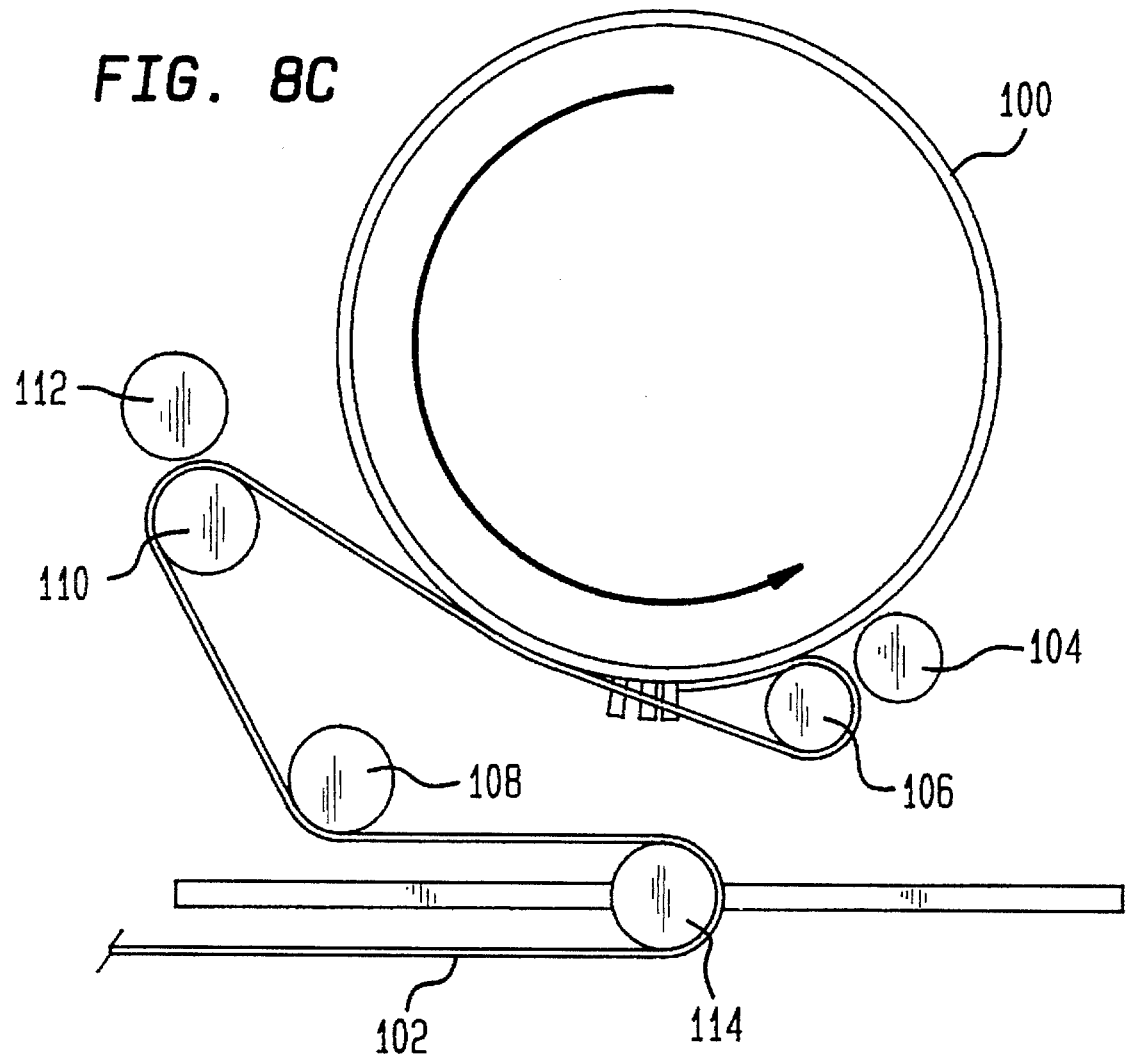

VERSATILE RECONFIGURABLE GANTRY FOR USE IN SCINTILLATION CAMERA SYSTEMS

BACKGROUND OF THE INVENTION

The invention relates to nuclear medicine, and more particularly relates to gantries for scintillation cameras. In its most immediate sense, the invention relates to scintillation camera gantries of the two detector (hereinafter, "dual-head") type.

A dual-head scintillation camera should provide the clinician with the option of conducting SPECT (Single Photon Emission Computed Tomography) studies with the detectors ("heads") in two configurations. In one configuration, the heads should be at 180° with respect to each other while they rotate around the patient; in the other configuration, the heads should be at approximately 90° with respect to each other while they rotate around the patient. This is because conventional SPECT studies are conducted with the heads opposed to each other, while cardiac SPECT studies are most efficiently carried out with the heads forming a right angle.

Systems of this general type are already known. For example, the VERTEX camera manufactured by ADAC Laboratories has two detectors which can be opposed to each other or can be angulated at an angle of less than 180° with respect to each other while they rotate around the patient. However, known dual-head scintillation camera systems suffer from various disadvantages.

In particular, known dual-head scintillation camera gantries are insufficiently versatile and sometimes inconvenient to use. For example, the VERTEX camera is not well adapted to carry certain types of studies (e.g. studies in which the patient is standing or sitting). Additionally, it is difficult to transfer a patient from a gurney into the camera gantry.

It would be advantageous to provide a dual-head scintillation camera gantry which would permit the heads to be reconfigured between a 180° configuration and a 90° configuration, but which would nonetheless be able to carry out other types of studies (e.g. whole body bone scans).

It is accordingly one object of the present invention to provide a dual-head scintillation camera gantry which permits the heads to be reconfigured between 180° and 90° angulations and which also permits other types of studies to be carried out conveniently.

Another object of the invention is to provide such a gantry into which a patient can easily be transferred from a gurney.

Yet a further object of the invention is to provide such a gantry which is not only versatile but which can also be produced at reasonable cost.

Yet another object is, in general, to improve on known gantries of this general type.

In accordance with the invention, first and second scintillation camera detectors are provided and are mounted, respectively, to first and second yoke assemblies. The first yoke assembly is mounted to a ring gear which is rotatable within a vertical plane about a horizontal axis. The second yoke assembly is mounted to an annulus which is located within the ring gear and which is rotatable within the plane and about the axis. Means are provided for rotating the ring gear in said plane and about said axis and means are also provided for locking said first and second yoke assemblies together, whereby said first and second yoke assemblies rotate together when they are locked together and the first yoke assembly is being rotated by said rotating means.

Advantageously, and in accordance with the preferred embodiment of the invention, each detector is pivotally secured to its corresponding yoke assembly and each of the detectors is radially movable towards and away from the axis of the gantry. Furthermore, the entire gantry is laterally moveable.

A dual-head scintillation camera gantry in accordance with the invention is completely open along its axis. This permits whole body bone scans to be conducted by moving the patient axially while keeping the heads fixed. Additionally, by rotating the heads so their directions of view face parallel to the axis, sitting-patient studies can be conducted by placing the patient in front of one of the heads and keeping the gantry fixed in position. In SPECT studies where the heads do not orbit circularly with respect to the patient axis (so-called NCO or Non-Circular Orbit studies), the NCO feature can be conveniently accomplished by moving the patient up and down and/or moving the gantry laterally while the heads rotate around the patient. This has the advantage that a patient remains laterally fixed in position during the study. The patient is therefore less likely to be disoriented or disturbed by movement during the study.

In accordance with the invention, only one motor drive is required to accomplish the functions of head reconfiguration and head rotation. This reduces the standard cost of the resulting gantry. Furthermore, because the second yoke assembly is mounted to an annulus located within the first yoke assembly, a single-head scintillation camera gantry can be produced merely by omitting various parts and making only minor modifications to the gantry structure. In other words, the invention constitutes an easily-modified platform which may be used "as is" for a dual-head gantry or modified to produce a single-head gantry.

BRIEF DESCRIPTION OF THE DRAWINGS

The invention will be better understood with reference to the following illustrative and non-limiting drawings, in which:

FIGS. 8A, 8B and 8C show the cable-handling mechanism which is used in the preferred embodiment of the invention.

DETAILED DESCRIPTION OF PREFERRED EMBODIMENTS

Figure 1:
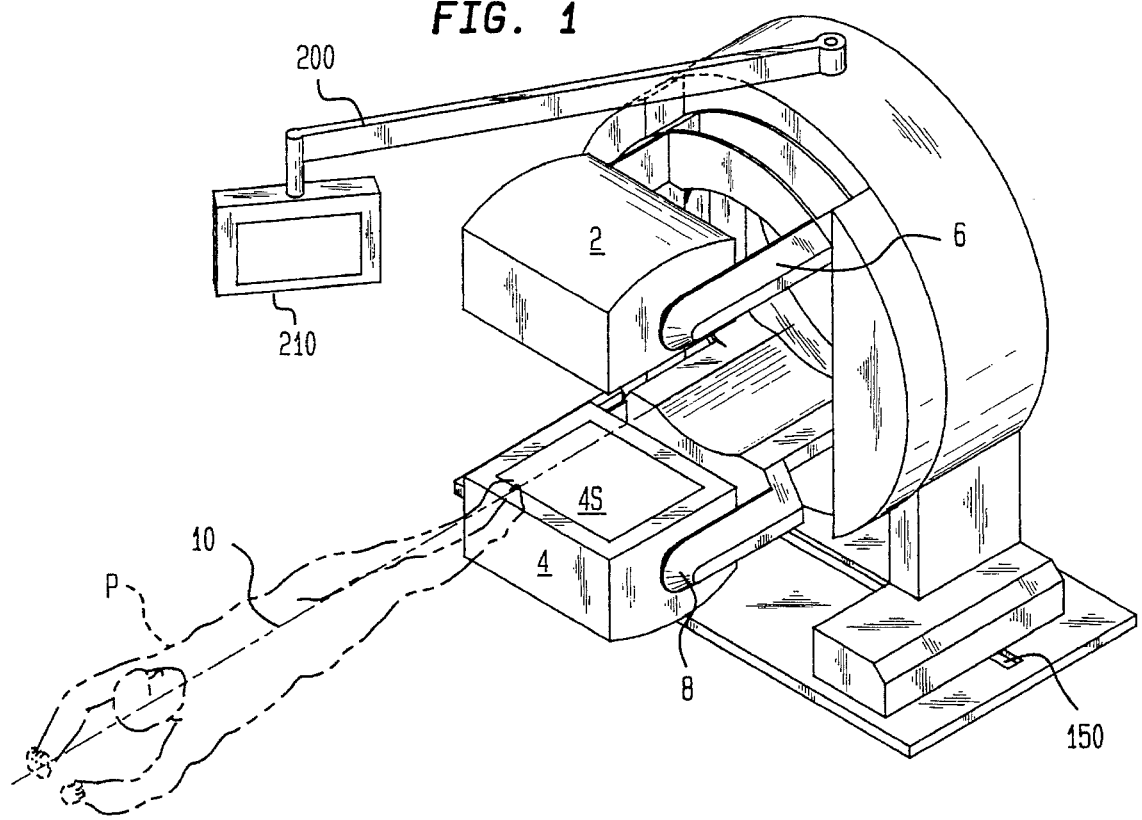
FIG. 1 shows a preferred embodiment of the invention in the 180° configuration.
Figure 2:
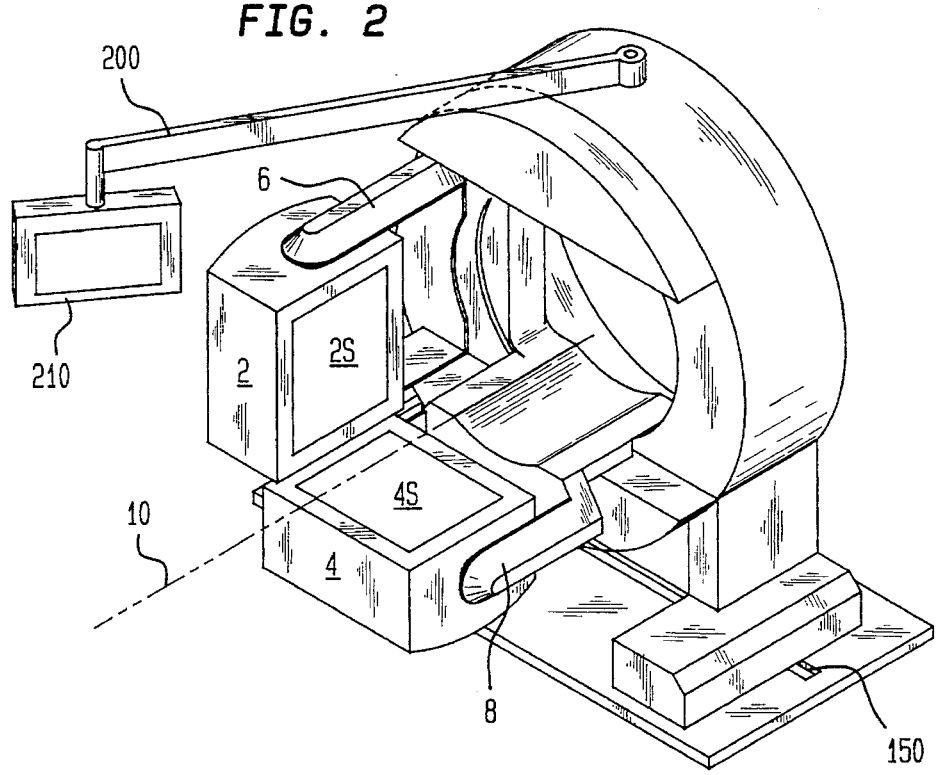
FIG. 2 shows the preferred embodiment in the 90° configuration.

Referring first to FIGS. 1 and 2, there is shown a first detector 2 and a second detector 4. The detectors 2 and 4 are known by themselves; they convert gamma radiation (not shown) which is incident upon their sensitive regions 2S and 4S into electrical signals which are eventually routed to a computer (not shown) and used to reconstruct an image of a patient P. (As shown, the patient P is aligned with the axis 10 of the preferred embodiment, but this is not necessarily always so. This will become clear below when the NCO feature of the preferred embodiment is described.) As shown, the detectors 2 and 4 are rectangular; this is preferred, but not required. The detectors can alternatively be circular. As shown, there are no collimators on the detectors 2 and 4. This is to simplify the drawings; in use, a collimator would be mounted to each of the detectors 2 and 4.

The first detector 2 and the second detector 4 are respectively secured to a first yoke assembly generally indicated by reference numeral 6 and a second yoke assembly generally indicated by reference numeral 8. (The first yoke assembly 6 and the second yoke assembly 8 will be described in more detail below.) The yoke assemblies 6 and 8 can rotate to a maximum of 540° around the axis 10 of the gantry, permitting SPECT studies to be carried out on the patient P from a variety of initial positions of the detectors 2 and 4. For conventional SPECT studies, the 180° configuration illustrated in FIG. 1 is utilized. In this configuration, the first detector 2 and the second detector 4 face each other, as do the sensitive surfaces 2S and 4S. However, cardiac SPECT studies are advantageously carried out using the 90° configuration illustrated in FIGS. 2. In this configuration, the sensitive surfaces 2S and 4S are at right angles. (As will be discussed below, the angle between the first detector 2 and the second detector 4 need not be exactly 90° degrees; the preferred embodiment provides for angles of between 70° and 90°.)

For e.g. whole body bone scans, wherein the patient P is scanned from toe to head or vice versa, the FIG. 1 180° configuration is used and the patient P is supported on a horizontally moveable pallet (not shown) which is aligned with the axis 10. Then, the pallet is moved along the axis 10 for a distance sufficient to make sure that all portions of the patient's body pass between the detectors 2 and 4.

Figure 3:
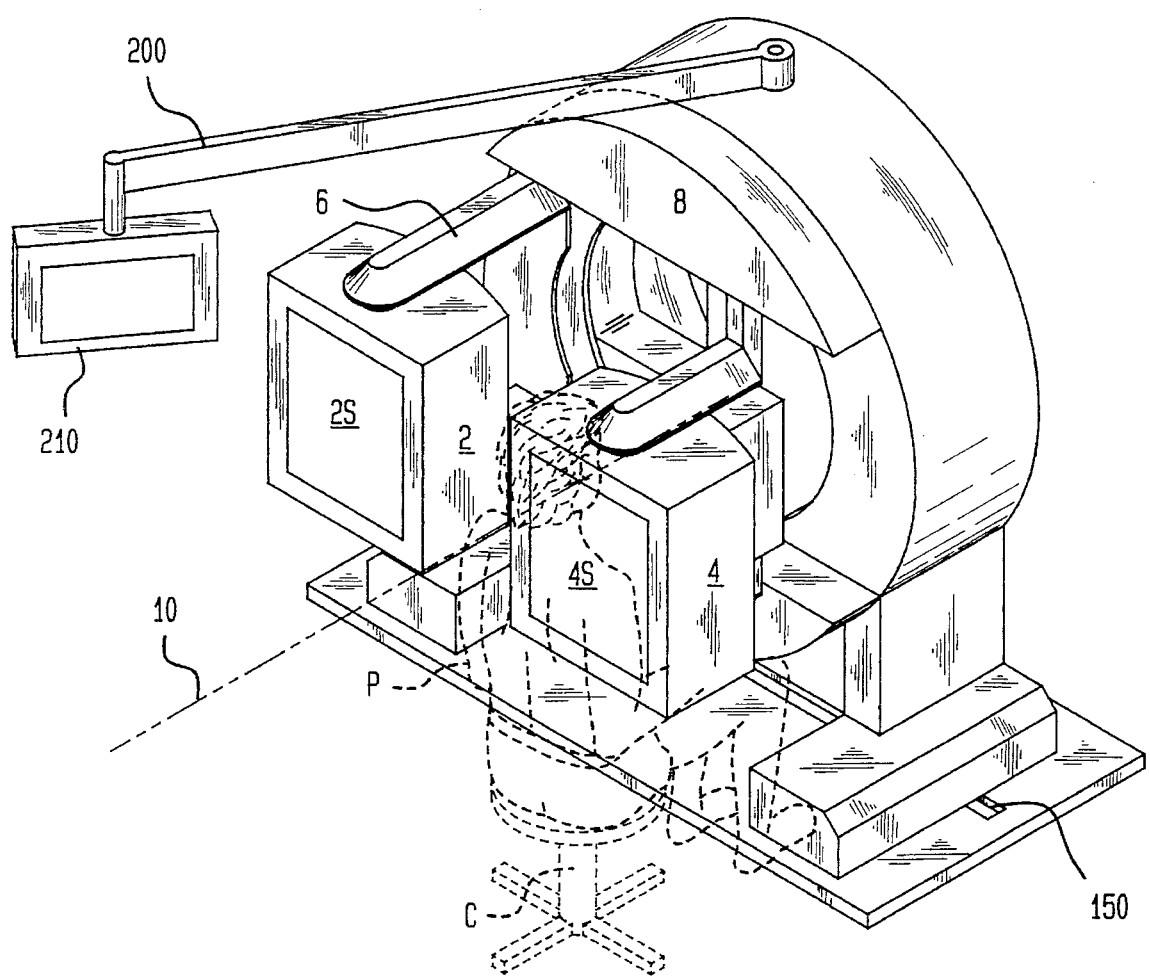
FIG. 3 shows the preferred embodiment configured for use in a sitting-patient study.

In accordance with the preferred embodiment, the detectors 2 and 4 are pivotally secured (see FIG. 3) to the yoke assemblies 6 and 8. This permits the detectors to be rotated (in cardiac imaging, this type of rotation is referred to as "caudal tilt") so their sensitive crystal surfaces 2S and 4S become coplanar. The patient P may then be seated on a chair C directly in front of the gantry and one of the detectors 2 or 4. Alternatively, the patient P may stand with his chest in front of one of the detectors 2 or 4; this alternative is not shown in FIG. 3.

It can thus be seen that the preferred embodiment of the invention is capable of performing conventional 180° SPECT studies, 90° cardiac SPECT studies, whole body bone scans, and sitting-patient studies. (Quite obviously, the preferred embodiment of the invention is also capable of planar imaging studies of a prone or supine patient, but such studies will not be described here because in such studies the gantry is held fixed with the detectors 2 and 4 in the 180° configuration illustrated in FIG. 1.)

The first and second yoke assemblies 6 and 8 will now be described with reference to FIGS. 4 and 5. It will be understood that FIGS. 4 and 5 have been simplified for clarity and that much necessary structure (e.g. the mechanical structures needed for caudal tilting of the detectors 2 and 4, the overall support structures for the gantry, the electronic control systems) is not shown therein. However, such structure is not part of the invention and is known to persons skilled in the art.

Figure 4:
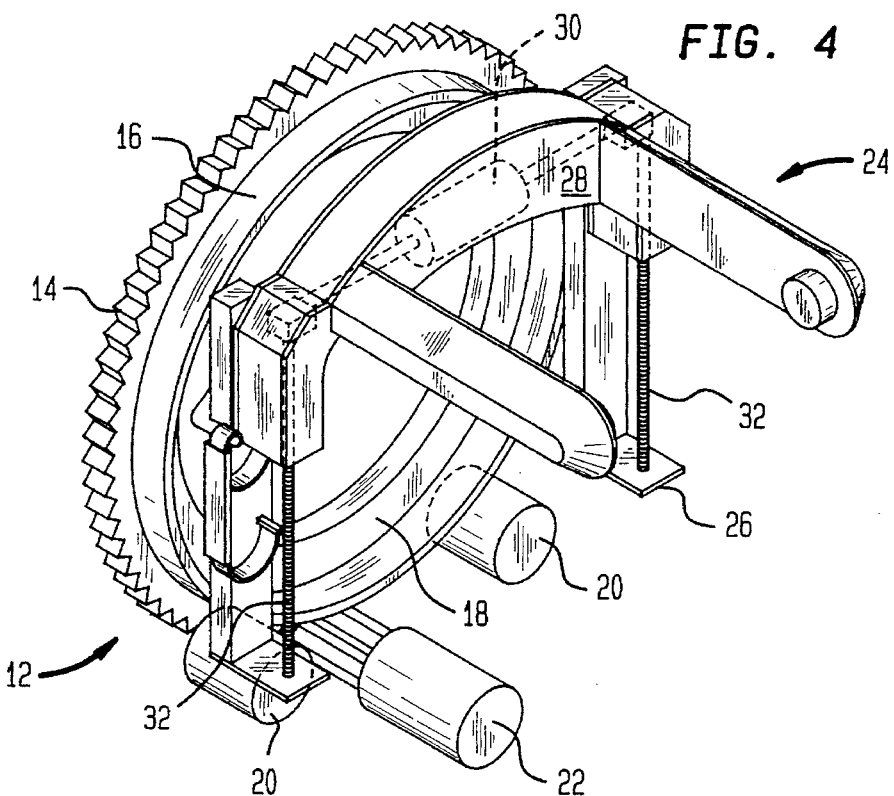
FIG. 4 shows a schematized perspective view of the first yoke assembly.

The first yoke assembly 6 as is schematically illustrated in FIG. 4 is fixed to, and rotates with, a ring gear generally indicated by reference numeral 12. The ring gear 12 rotates in a vertical plane about the axis 10. The ring gear 12 has a rear gear 14 and a cylindrical flange 16 which extends forwardly from the rear gear 14; the rear gear 14 and the flange 16 are coaxial with the axis 10. The ring gear 12 also has an annular rim 18 which extends radially inwardly from the flange 16. (As shown, the rear gear 14, the flange 16 and the rim 18 are all integral parts of the ring gear 12, but this is not necessary and different parts may be joined together as by welding or the use of fasteners.)

Two spaced-apart rollers 20 are rotatably secured to the frame (not shown) and the flange 16 rests upon them. In this way, the rollers 20 support the ring gear 12 and the first yoke assembly 6 for rotation about the axis 10. A drive motor 22 is operatively secured to the rear gear 14 for rotating the ring gear 12. (As illustrated, the motor 22 is in line with a speed reducer which drives the ring gear 14, but this is not necessary. A direct drive, a belt drive, a transmission drive, or some combination of these elements, may be used instead. The mechanism by which the ring gear 12 is rotated is not a part of the invention.)

Another part of the first yoke assembly 6 is the first detector carriage generally indicated by reference number 24. The function of the carriage 24 is to move the detector 2 radially with respect to the axis 10.

The frame 26 of the carriage 24 is fixed with respect to the flange 16. As a result, when the ring gear 12 rotates, the carriage 24 rotates with it. A first yoke 28 is slidably attached to the frame 24 and moves with respect thereto on a linear bearing (not shown). The yoke 28 supports the detector 2. Within the yoke 28 is a drive motor 30 which is operatively connected to a pair of power screws 32. The power screws 32 are rotatably secured within the frame 26 and engage threaded nuts (not shown) which are fixed with respect to the yoke 28. When the motor 30 is operated, the yoke 28 moves radially with respect to the frame 26 and therefore moves radially with respect to the axis 10. The direction of this radial movement is determined by the direction in which the motor 30 is rotated.

To summarize, the first yoke assembly 6 is used to rotate the detector 2 and to move the detector 2 radially. These two motions may be carried out independently (and indeed simultaneously) by operation of the motors 22 and 30.

Figure 5:
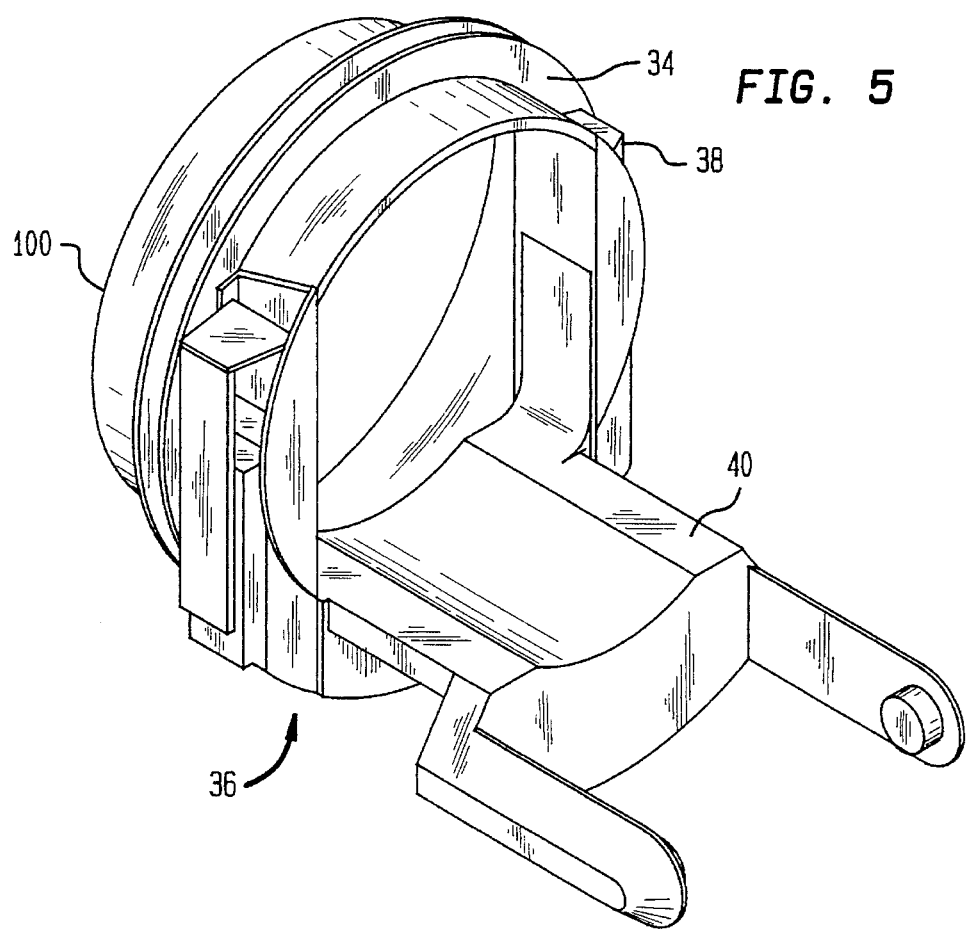
FIG. 5 shows a schematized perspective view of the second yoke assembly.

Turning now to the second yoke assembly 8 as shown in FIG. 5, there is shown an annulus 34 which is dimensioned to fit within the rim 18 of the first yoke assembly 6. (There is a bearing race between the annulus 34 and the rim 18, but this race has been omitted from the Figures for clarity.) To the annulus 34 is fitted a second detector carriage which is generally indicated by reference number 36. The carriage 36 has a frame 38 which is fixed to the annulus 34. A second yoke 40 supports the detector 4. The second yoke 40 is slidably mounted to the frame 38 by linear bearings (not shown) and is likewise radially moveable by a motor-driven pair of power screws (not shown). The second yoke assembly 8 performs for the detector 4 the same functions performed by the first yoke assembly 6 for the detector 2; the detector 4 can be rotated and can also moved radially, and can carry out these motions independently of each other.

The operation of the preferred embodiment will now be described for two modes: the SPECT study mode and the reconfigure mode. In the SPECT study mode, the detectors 2 and 4 rotate together about the axis 10. In the reconfigure mode, the detector 4 is held fixed and the detector 2 is rotated to the desired position. The SPECT study mode will be described first.

As stated above, a SPECT study requires that the detectors 2 and 4 be rotated about the axis 10. (For a conventional dual-head non-cardiac SPECT study, the rotation will be 180°; for a conventional dual-head cardiac SPECT study, the rotation will usually, but not always, be 90°.) In the SPECT study mode, the annulus 34 is locked to the rim 18 using a mechanism described below and schematically illustrated in FIGS. 6A and 6B. This mechanism locks the yoke assemblies 6 and 8 together. Then, the motor 22 is operated. As a result, both detectors 2 and 4 are rotated about the axis 10.

Figure 6:
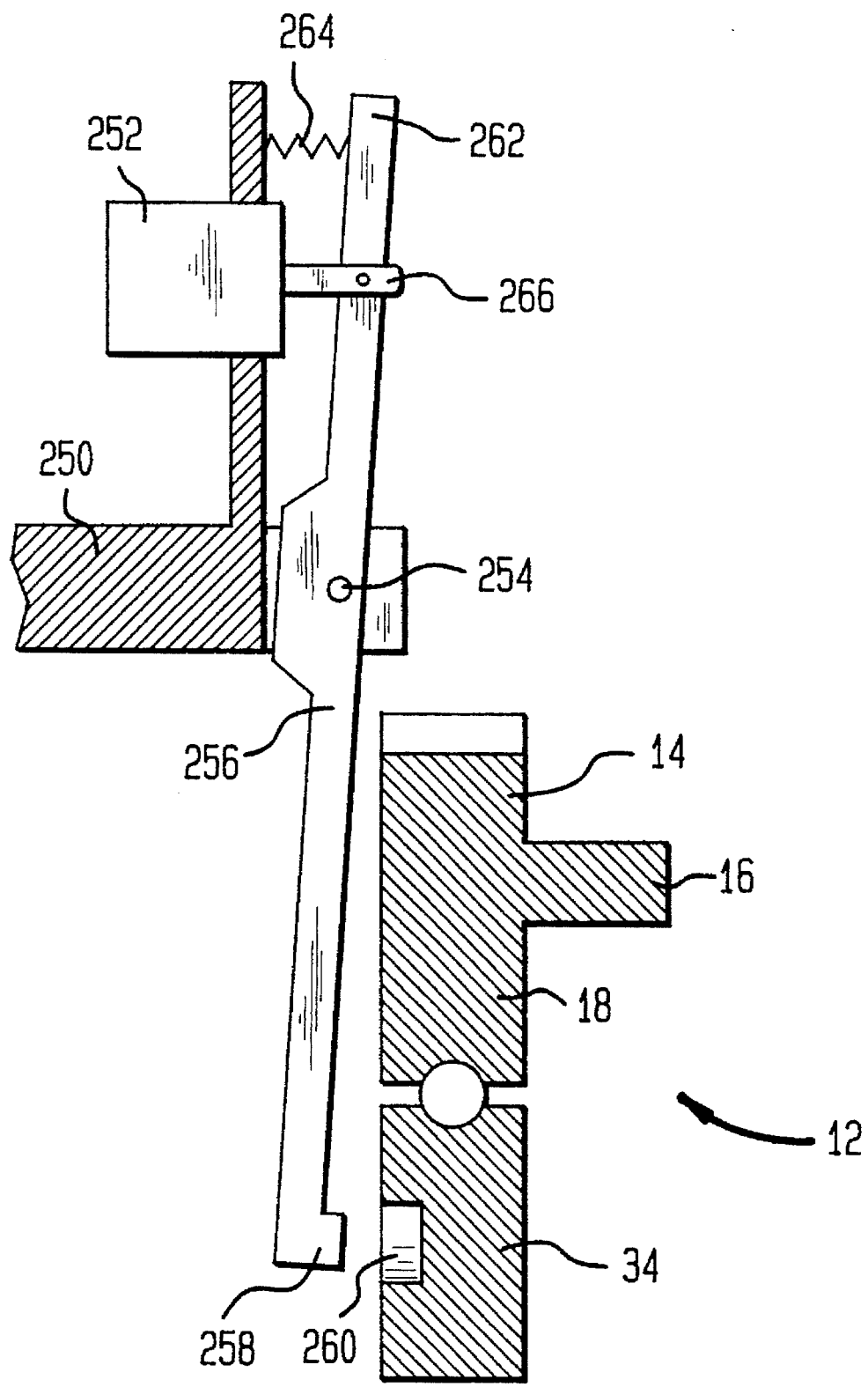
FIG. 6 shows a schematized view of the apparatus which brakes the second yoke assembly.
Figure 7A:
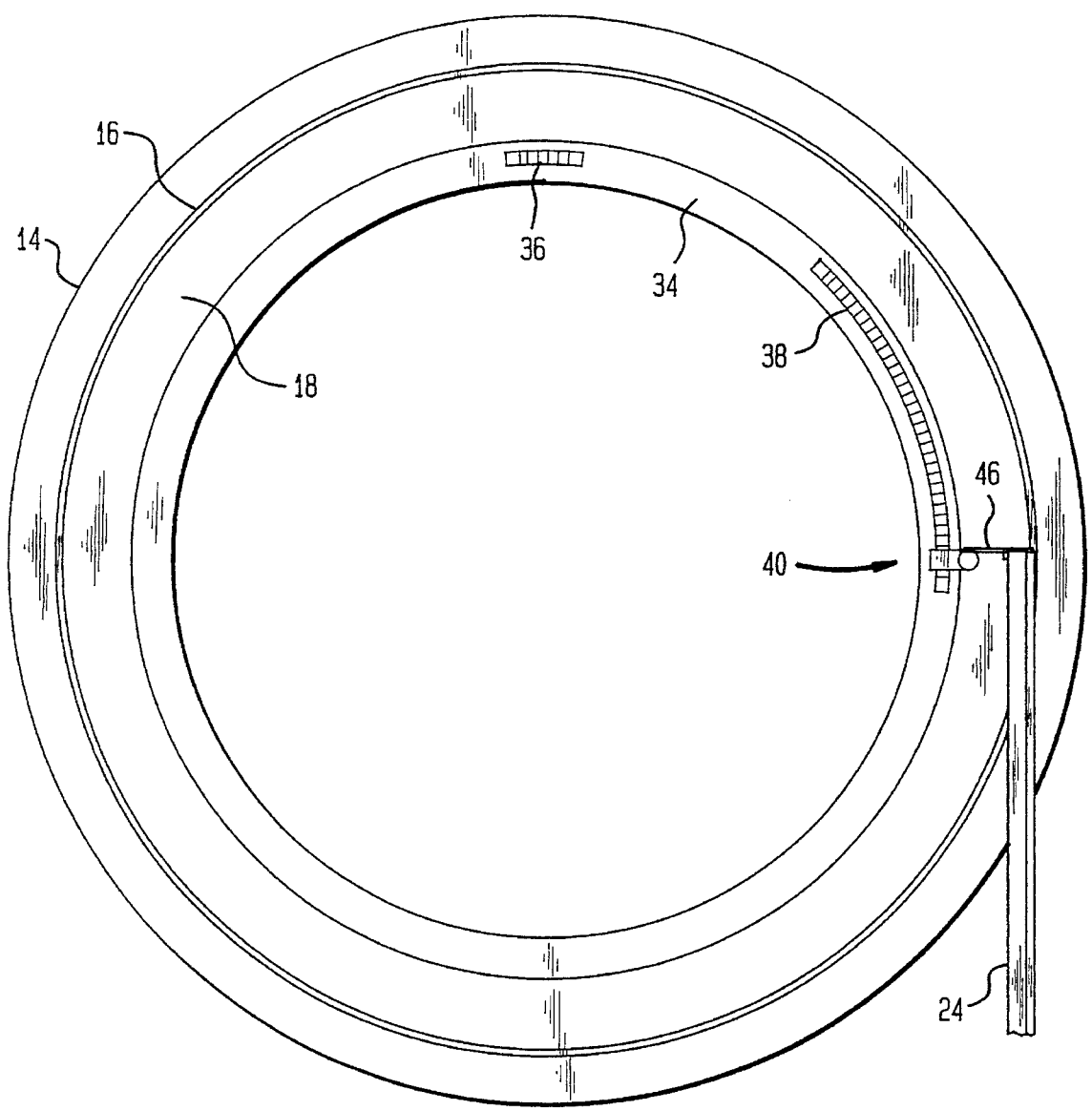
FIGS. 7A and 7B are schematized views of the locking mechanism which locks and unlocks the yoke assemblies.
Figure 7B:
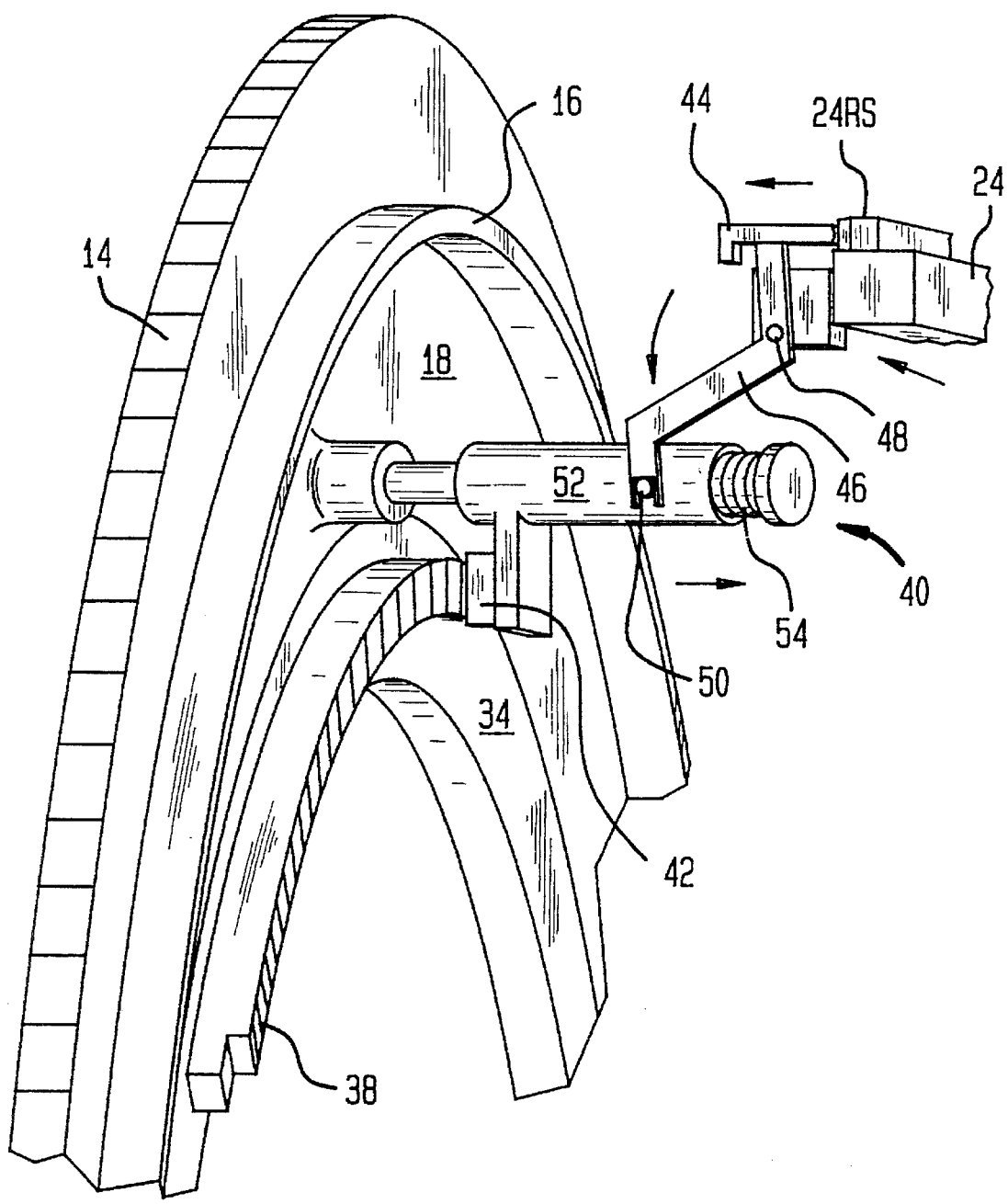

The reconfigure mode has an initial step, an intermediate step, and a final step. In the initial step of reconfigure mode, the motor 20 is operated to bring the second detector 4 to its lowest position (this is the position illustrated in FIGS. 1 and 2.) This position minimizes torsional forces produced by the force of gravity acting on the second detector 4. In this step, the yoke assemblies 6 and 8 are locked together, so both detectors 2 and 4 rotate about the axis 10. Then, the second yoke assembly 8 is braked, and thereby held fixed. The apparatus by which this takes place is shown in FIG. 6 and will be described below. Once this has occurred, the intermediate step takes place. In the intermediate step, the below-described mechanism illustrated in FIGS. 7A and 7B is unlocked so the first yoke assembly 6 becomes free to rotate with respect to the second yoke assembly 8. Furthermore, the motor 22 is operated in the appropriate direction to rotate the first detector 2 to the proper position. (If, for example, the invention were to be reconfigured to the FIG. 2 90° configuration from the FIG. 1 180° configuration, the motor 22 would be operated to drive the first detector 2 counterclockwise as viewed in FIGS. 1 and 2. Reconfiguration from the FIG. 2 90° configuration to the FIG. 1 180° configuration would require rotation of the motor 22 in the opposite sense and clockwise rotation of the detector 2.) Thereafter, in the final step, the mechanism illustrated in FIGS. 7A and 7B is locked once again, permitting operation in the SPECT study mode.

The apparatus for braking the second yoke assembly 8 will now be described in connection with FIG. 6. In general, this apparatus works by mechanically connecting the annulus 34 to the fixed frame of the gantry when the annulus 34 is to be held in position and releasing this connection when the annulus 34 is to be free to rotate.

The fixed frame 250 of the gantry supports a solenoid 252 and a pivot 254. A lever 256 pivots about the pivot 254. The lower end 258 of the lever 256 is shaped to engage with a mating recess 260 in the annulus 34; the upper end 262 of the lever 256 is biased by compression spring 264 which urges the upper end 262 away from the frame 250. When the solenoid 252 is unenergized, the compression spring 264 urges the lower end 258 to be out of engagement with the recess 260.

When the second yoke assembly 8 is at the proper position and is to be braked, the solenoid 252 is energized. The armature 266 of the solenoid 252 the pivots the lever 256 against the pressure of the spring 264 and urges the lower end 258 to engage with the recess 260. This brakes the annulus 34, and thus holds the second yoke assembly 8 in position. When the second yoke assembly 8 is to be free to rotate, the solenoid 252 is deenergized, causing the spring 264 to pivot the lever 256 about the pivot 254 and causing the lower end 258 to be disengaged from the recess 260.

Referring now to FIGS. 7A and 7B, it can be seen that the annulus 34 supports two toothed elements 36 and 38. The elements 36 and 38 are fixed to the annulus 34 and rotate with it. FIG. 7B shows a mechanism 40, which is secured to the rim 18 and rotates with it. The mechanism 40 has a toothed element 42. When the mechanism 40 is unlocked, the element 42 is disengaged from the elements 36 and 38 and rim 18 is therefore free to rotate with respect to annulus 34.

However, when the mechanism 40 is locked, the element 42 will be engaged with one of the elements 36 and 38. When the element 42 is engaged with the element 36, the detectors 2 and 4 will be in the 180° configuration illustrated in FIG. 1. When the element 42 is engaged with the element 38, the detectors 2 and 4 will be in the 90° configuration illustrated in FIG. 2. As can be seen in FIG. 7A, the element 38 subtends an angle of approximately 20°; this permits the detector 2 to be angled anywhere between 70° and 90° with respect to the detector 4 when in the configuration illustrated in FIG. 2. (The 20° subtended by the element 38 is not a part of the invention. Alternatively, the element 38 could subtend an angle as large as 90°. The size of the element 38 is determined by trading off cost against the benefit of having a wider range of angulation between the detectors 2 and 4.)

It will be apparent that the element 42 is engaged with and disengaged from the elements 36 and 38 by moving the element 42 normal to the annulus 34. This in turn is carried out by moving the first detector carriage 24 to an extreme position which is outside its normal range of motion. When the carriage 24 is moved to an extreme upward position, the right shoulder 24RS of the carriage 24 strikes the cam follower 44. Because the right shoulder 24RS is sloped to form a cam, the cam follower 44 moves toward the rim 18. This pivots the lever 46 about the pivot 48. The end 50 of the lever 46 engages with a pushrod 52 which is biased towards the annulus 34 by a spring 54. The element 42 is mounted to that end of the pushrod 52 which is remote from the spring 54. Thus, when the carriage 24 is moved to an extreme upward position, the shoulder 24RS strikes the cam follower 44, the cam follower 44 rotates the lever 46 and the lever 46 pulls the pushrod 52 against the spring 54. This causes the element 42 to become disengaged from whichever element (36 or 38) it was previously engaged with. The first yoke assembly 6 can then be rotated so that the element 42 is positioned to engage with the other element (38 or 36). Thereafter, the carriage 24 is moved away from its extreme upward position. The spring 54 then urges the element 42 to engage with the other element, which causes a corresponding rotation of the lever 46 and a corresponding movement of the cam follower 44.

The FIGS. 7A and 7B mechanism is normally locked and is only unlocked when the carriage 24 has been moved to an extreme position outside its normal range of motion.

The preferred embodiment of the invention allows the detectors 2 and 4 to be rotated through an angle of 530°. This is accomplished using a cable handling system which is schematically illustrated in FIGS. 8A, 8B and 8C, which will now be discussed.

A drum 100 is mounted to the annulus 34 on the other side of the second yoke carriage 36. A cable 102 (which permits electrical connections to inter alia the detectors 2 and 4) is fixed to the drum 100. Two stationary rollers 104 and 106 are also fixed to the drum; the cable 102 passes under the roller 106 and between the rollers 104 and 106.

Figure 8A:
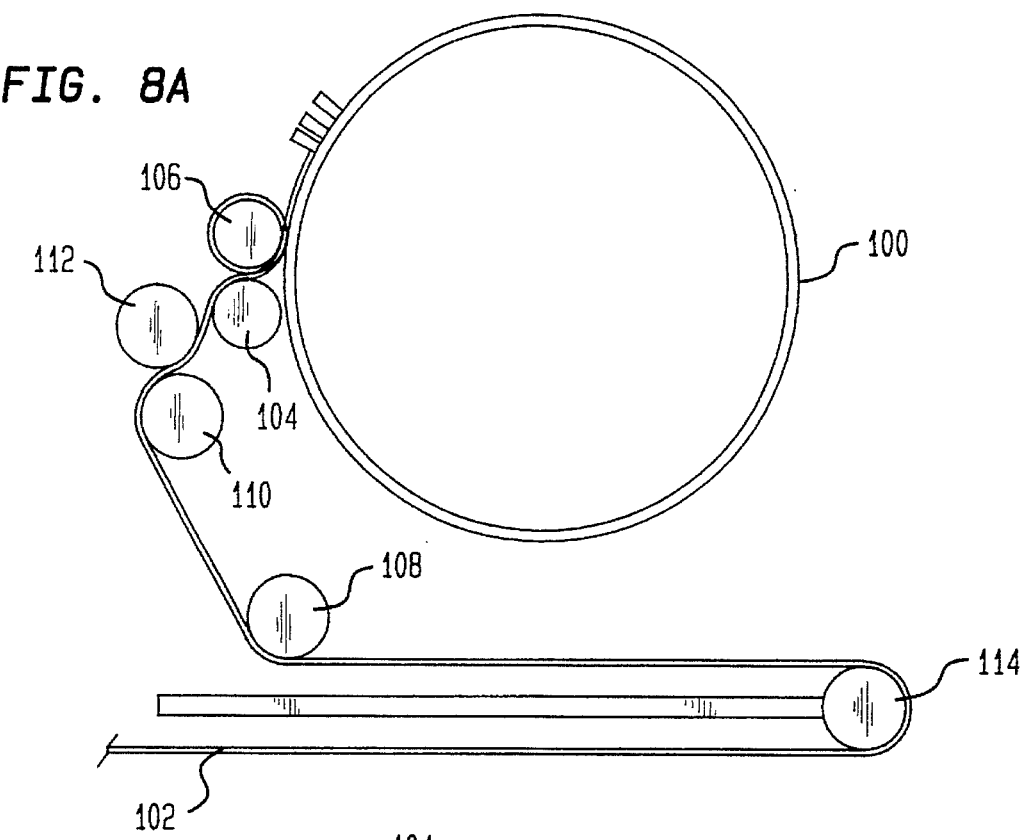
Figure 8B:
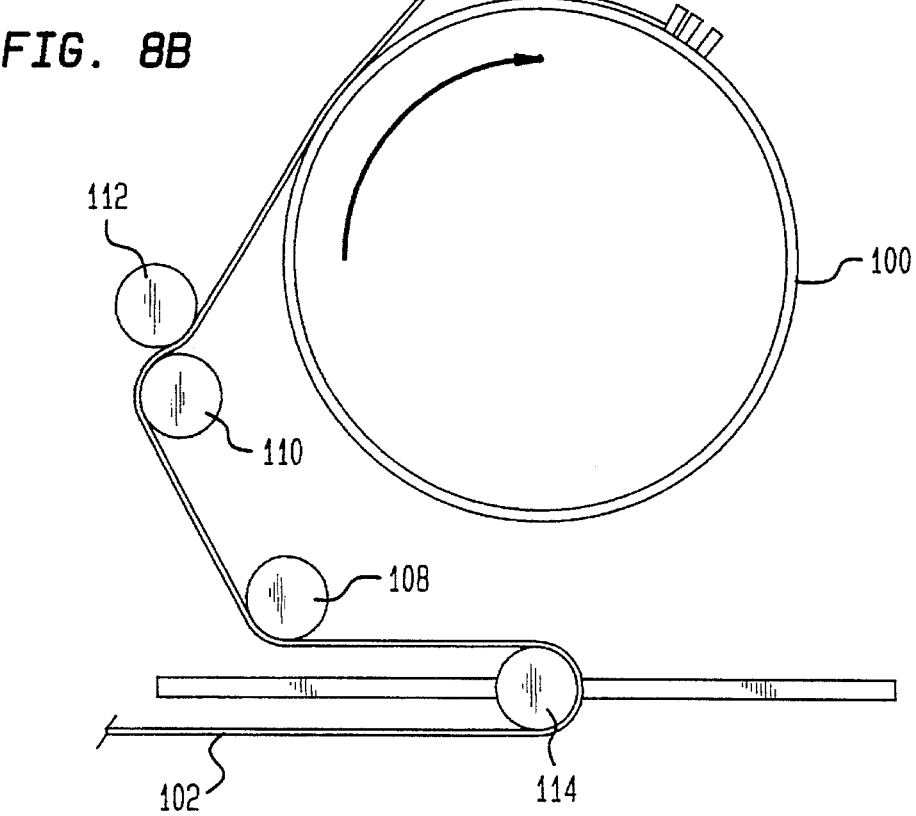

The cable 102 also passes through a takeup mechanism which includes an idler roller 108, two feed rollers 110 and 112, and a spring-loaded takeup roller 114 which is urged to the right as viewed in FIGS. 8A, 8B and 8C. After passing between the rollers 104 and 106, the cable is routed between the rollers 110 and 112 and thence around the roller 108. After passing around the roller 108, the cable passes around the takeup roller 114, from whence it is routed to a fixed point on the chassis (not shown).

When, as shown in FIG. 8B, the second detector is rotated counterclockwise as shown in FIGS. 1 and 2 (this corresponds to clockwise as viewed in FIG. 8B) from the initial position shown in FIG. 8A, the cable 102 is wound over the roller 104 and the takeup roller 114 is moved to the left as viewed in FIG. 8B. Eventually, the cable 102 is laid down upon the drum 100 and wrapped around it as rotation continues. Alternatively, opposite rotation such as is shown in FIG. 8C causes the same thing to happen, but in this instance the cable 102 is wrapped around the roller 106.

The NCO (non-circular orbit) feature of the preferred embodiment will now be described. NCO is used to compensate for problems which come about when a detector of a scintillation camera follows a circular orbit around the body of a patient.

A patient's body is not circular in cross-section, so when a detector follows a circular orbit around the patient's body there are orbit positions ("stations") where the detector may be relatively distant from the body of the patient. It is known that resolution decreases with increasing spacing between the patient and the detector. Therefore, the use of a circular detector orbit diminishes resolution at certain orbit stations and degrades the quality of the data acquired during the study.

To avoid this disadvantage, it is known to use an elliptical or otherwise noncircular orbit so the detector orbit more accurately corresponds to the cross-sectional shape of the patient and thereby keeps more constant the patient—detector spacing. This can be done by varying the radial position of the detector as it rotates around the patient, by moving the patient bed, or both.

The preferred embodiment of the present invention proceeds from the realization that lateral movement of the patient is undesirable. Such movement can make the patient feel ill or uncomfortable or can itself cause undesirable patient motion. In accordance with the preferred embodiment of the invention, and as shown in FIG. 1, a means 150, such as an power screw, is provided for moving the entire gantry laterally, i.e. moving the axis 10 in a horizontal plane. It will be recalled that each of the detectors 2 and 4 has a radial degree of freedom. By providing the gantry with the above-described lateral degree of freedom, and utilizing lateral motion of the gantry as the detectors 2 and 4 rotate about the patient, it is possible to cause the detectors 2 and 4 to orbit the axis 10 in a noncircular (e.g. elliptical) manner without moving the patient from side to side.

In the preferred embodiment, the detectors 2 and 4 are at their maximum radial positions when they are in the 90° configuration. This keeps the overall size of the gantry as small as possible.

In accordance with the preferred embodiment, there is provided a boom 200 which is attached to the top of the gantry and which supports a control panel 210 at its distal end. The boom 200 is rotatable in a horizontal plane about its proximal end, and the control panel 210 is rotatable about its vertical central axis. This permits a technician to move the boom 200 and panel 210 so as to have access to the control panel 210 regardless of the side of the gantry at which the technician is located. The control panel 210 includes controls and displays for, inter alia, reconfiguring and operating the gantry and adjusting the gantry to carry out various types of studies.

Although a preferred embodiment has been described above, the scope of the invention is limited only by the following claims:

We claim:

1. A dual-head scintillation camera gantry, comprising:

first and second scintillation camera detectors;

a first yoke assembly, the first yoke assembly being mounted to a ring gear which is rotatable within a vertical plane about a horizontal axis and the first yoke assembly having means for securing the first scintillation camera detector thereto;

a second yoke assembly, the second yoke assembly being mounted to an annulus which is located within said ring gear and which is rotatable within said plane and about said axis, the second yoke assembly further having means for securing the second scintillation camera detector thereto;

means for rotating the ring gear in said plane and about said axis; and means for locking said first and second yoke assemblies together, whereby said first and second yoke assemblies rotate together when they are locked together and the first yoke assembly is being rotated by said rotating means.

2. The gantry of claim 1, further comprising first and second means for moving a scintillation camera detector radially towards and away from said axis, and wherein said first moving means is connected to the first yoke assembly and the second moving means is connected to the second yoke assembly.

3. The gantry of claim 1, wherein each detector is pivotally secured to its corresponding yoke assembly.

4. The gantry of claim 1, further comprising a brake for fixing the second yoke assembly in position while the first yoke assembly is rotated.

5. The gantry of claim 2, wherein the locking means is operatively connected to the first moving means in such a manner that said locking means is unlocked when the first moving means is moved to an extreme position and said locking means is locked when the first moving means is moved to a position which is elsewhere than said extreme position.

6. The gantry of claim 1, wherein said locking means allows the first and second yoke assemblies to be locked together in at least first and second configurations, the scintillation camera detectors being at 180° with respect to each other when in the first configuration and being at approximately 90° with respect to each other when in the second configuration.

7. The gantry of claim 1, further comprising means for laterally moving said first and second yoke assemblies, said first and second detectors, said rotating means and said locking means.

8. The gantry of claim 6, wherein said yoke assemblies can be angled between 70° and 90° when in said second configuration.

* * * * *